United States Patent [19]

Kvita et al.

[11] Patent Number: 5,011,944
[45] Date of Patent: Apr. 30, 1991

[54] SUBSTITUTED ALPHA-PYRONES

[75] Inventors: Vratislav Kvita, Reinach; Marcus Baumann, Basel; Walter Fischer, Reinach; Carl W. Mayer, Riehen, all of Switzerland; Thomas Allmendinger, Steinen, Fed. Rep. of Germany

[73] Assignee: Ciba-Geigy Corporation, Ardsley, N.Y.

[21] Appl. No.: 356,825

[22] Filed: May 24, 1989

[30] Foreign Application Priority Data

May 27, 1988 [CH] Switzerland ............... 2008/88
Jul. 19, 1988 [CH] Switzerland ............... 2753/88

[51] Int. Cl.$^5$ ............................. C07D 309/32
[52] U.S. Cl. ........................... 549/214; 549/291; 549/292; 549/293; 549/294; 568/328; 560/51; 560/150; 560/152; 560/156; 560/160; 560/183; 560/205
[58] Field of Search ............. 549/291, 214, 292, 293, 549/294

[56] References Cited

U.S. PATENT DOCUMENTS 2,334,180 11/1943 Elderfield et al. ............... 549/291
4,617,151 10/1986 Mayer et al. ..................... 540/1

OTHER PUBLICATIONS

CA 89:512077
Angew. Chem. 26(1987), No. 8.

Primary Examiner—Frederick E. Waddell
Assistant Examiner—Amelia A. Owens
Attorney, Agent, or Firm—Stephen V. O'Brien; Michael W. Glynn

[57] ABSTRACT

α-Pyrones of the formula I

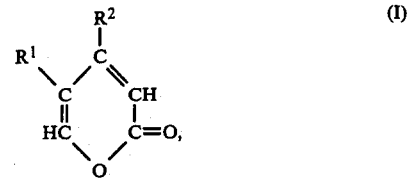

in which $R^1$ is —CF$_3$ or —COOR$^3$ and $R^3$ is the radical of a $C_1$-$C_{18}$ alcohol diminished by a hydroxyl group, and $R^2$ is —F, —Br, —Cl, —CN, —CF$_3$, $C_1$-$C_{18}$alkyl, $C_2$-$C_{18}$alkenyl, $C_2$-$C_{18}$alkynyl, $C_1$-$C_{18}$alkoxy, $C_1$-$C_{18}$alkylthio, $C_1$-$C_{18}$alkylsulfonyl, $C_6$-$C_{16}$aryl, $C_7$-$C_{24}$alkaryl, $C_7$-$C_{12}$aralkyl, $C_8$-$C_{24}$alkaralkyl, $C_6$-$C_{16}$aryloxy, $C_6$-$C_{16}$arylthio, $C_6$-$C_{16}$arylsulfonyl, $C_7$-$C_{24}$alkaryloxy, $C_7$-$C_{24}$alkarylthio, $C_7$-$C_{24}$alkarylsulfonyl, $C_7$-$C_{12}$aralkyloxy, $C_7$-$C_{12}$aralkylthio, $C_7$-$C_{12}$aralkylsulfonyl, $C_8$-$C_{24}$alkaralyloxy, $C_8$-$C_{24}$alkaralylthio, $C_8$-$C_{24}$alkaralylsulfonyl, secondary amine having 2 to 24 C atoms or trialkylsilyl or trialkoxysilyl each of which has 3 to 18 C atoms. They are suitable for the preparation of naphtho-1,4-quinones and anthra-1,4-quinones, from which tetrathiotetracenes or tetraselenotetracenes having electrochromic properties can be obtained.

5 Claims, No Drawings

SUBSTITUTED ALPHA-PYRONES

The invention relates to 4-substituted α-pyrone-5-carboxylic acid esters or 5-trifluoromethyl-α-pyrones and to 7-substituted naptho-1,4-quinone-6-carboxylic acid esters or 6-trifluoromethylnaphtho-1,4-quinones and to substituted butadienedicarboxylic acid esters.

α-Pyrone-5-carboxylic acid esters are known, see, for example, H. Gault et al, C.r. Acad. Sci. Paris Ser. C, 266. pages 131–134 (1968). α-Pyrone-4,5-dicarboxylic acid diesters are described in U.S. Pat. No. 4,617,151.

Other α-pyrone-5-carboxylic acid esters which are unsubstituted in the 3,6-position and substituted in the 4-position are not known. It has now been found that α-pyrones of this type can be obtained in a simple manner by reacting allenedicarboxylic acid esters with organometallic compounds to give propenedicarboxylic acid diesters which are substituted in the 2-position, reacting the latter with formic acid esters to give 1-alkoxymethylenebutadiene-2,4-dicarboxylic acid esters which are substituted in the 3-position and cyclizing the latter to give α-pyrones.

The invention relates to compounds of the formula I

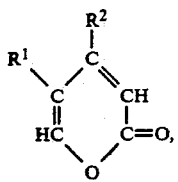

in which $R^1$ is —$CF_3$ or —$COOR^3$ and $R^3$ is the radical of a $C_1$–$C_{18}$ alcohol diminished by a hydroxyl group, and $R^2$ is —F, —Br, —Cl, —CN, —$CF_3$, $C_1$–$C_{18}$alkyl, $C_2$–$C_{18}$alkenyl, $C_2$–$C_{18}$alkynyl, $C_1$–$C_{18}$alkoxy, $C_1$–$C_{18}$alkylthio, $C_1$–$C_{18}$alkylsulfonyl, $C_6$–$C_{16}$aryl, $C_7$–$C_{24}$alkaryl, $C_7$–$C_{12}$aralkyl, $C_8$–$C_{24}$alkaralkyl, $C_6$–$C_{16}$aryloxy, $C_6$–$C_{16}$arylthio, $C_6$–$C_{16}$arylsulfonyl, $C_7$–$C_{24}$alkaryloxy, $C_7$–$C_{20}$alkarylthio, $C_7$–$C_{24}$alkarylsulfonyl, $C_7$–$C_{12}$aralkyloxy, $C_7$–$C_{12}$aralkylthio, $C_7$–$C_{12}$aralkylsulfonyl, $C_8$–$C_{24}$alkaralkyloxy, $C_8$–$C_{24}$alkaralkylthio, $C_8$–$C_{24}$alkaralkylsulfonyl, secondary amine having 2 to 24 C atoms or trialkylsilyl or trialkoxysilyl each of which has 3 to 18 C atoms.

In a preferred subgroup, $R^2$ is —F, —Br, —Cl, —$CF_3$, $C_1$–$C_{18}$alkyl, $C_2$–$C_{18}$alkenyl, $C_1$–$C_{18}$alkoxy, $C_1$–$C_{18}$alkylthio, $C_1$–$C_{18}$alkylsulfonyl, $C_6$–$C_{10}$aryl, $C_7$–$C_{24}$alkaryl, $C_7$–$C_{12}$aralkyl, $C_6$–$C_{10}$aryloxy, $C_6$–$C_{10}$arylthio, $C_6$–$C_{10}$alkylsulfonyl, $C_7$–$C_{12}$aralkyloxy, $C_7$–$C_{12}$aralkylthio or $C_7$–$C_{12}$aralkylsulfonyl.

As the radical of an alcohol, $R^3$ preferably contains 1–12 C atoms, especially 1 to 6 C atoms. $R^3$ can, for example, be linear or branched alkyl, $C_5$cycloalkyl or $C_6$cycloalkyl each of which is unsubstituted or substituted by $C_1$–$C_6$alkyl, or $C_6$–$C_{12}$aryl or $C_6$–$C_{12}$aryl-$C_xH_{2x}$ each of which is unsubstituted or substituted by $C_1$–$C_6$alkyl and in which x is 1 to 4. Aryl is preferably phenyl and x is preferably 1. $R^3$ is preferably $C_1$–$C_{18}$alkyl, particularly $C_1$–$C_{12}$alkyl and especially $C_1$–$C_6$alkyl. Some examples are methyl, ethyl, the isomers of propyl, butyl, pentyl, hexyl, heptyl, octyl, nonyl, decyl, undecyl, dodecyl, tetradecyl, hexadecyl and octadecyl, cyclopentyl, cyclohexyl, methylcyclohexyl, phenyl, benzyl, methylphenyl, dimethylphenyl, ethylphenyl, methylethylphenyl, t-butylphenyl and methylbenzyl. It is particularly preferable for $R^3$ to be methyl or ethyl.

As alkyl, alkoxy, alkylthio and alkylsulfonyl, $R^2$ can be linear or branched and preferably contains 1 to 12 C atoms, particularly 1 to 6 C atoms and especially 1 to 4 C atoms. Examples are methyl, ethyl and the isomers of propyl, butyl, pentyl, hexyl, heptyl, octyl, nonyl, decyl, undecyl, dodecyl, tridecyl, tetradecyl, pentadecyl, heptadecyl and octadecyl and the corresponding alkoxy, alkylthio and alkylsulfonyl radicals.

As alkenyl and alkynyl, $R^2$ can be linear or branched and preferably contains 2 to 12 C atoms, particularly 2 to 6 C atoms. Some examples are vinyl, ethynyl, allyl, propargyl, prop-1-en-1-yl, but-1-en-4-yl, but-2-en-4-yl, pent-2-en-5-yl, hex-3-en-6-yl, but-2-yn-4-yl, pent-2-yn-4-yl, pent-2-yn-5-yl, hex-3-yn-5-yl and hex-3-yn-6-yl. $R^2$ as aryl or as a radical containing aryl is, for example, naphthyl or particularly phenyl. $R^2$ as alkaryl and the corresponding oxy, thio and sulfonyl radicals preferably contain 7 to 18 C atoms. $R^2$ as aralkyl and the corresponding oxy, thio and sulfonyl radicals preferably contain 7 or 8 C atoms. $R^2$ as alkaralkyl and the corresponding oxy, thio and sulfonyl radicals preferably contain 8 to 20 C atoms. In a preferred subgroup, $R^2$ as aryl or as a radical containing aryl is phenyl, phenoxy, phenylthio or phenylsulfonyl, $C_1$–$C_{12}$alkylphenyl, $C_1$–$C_{12}$alkylphenoxy, $C_1$–$C_{12}$alkylphenylthio or $C_1$–$C_{12}$phenylsulfonyl, $C_1$–$C_{12}$alkylphenyl—$C_nH_{2n}$—, $C_1$–$C_{12}$alkylphenyl—$C_nH_{2n}O$—, $C_1$–$C_{12}$alkylphenyl—$C_nH_{2n}S$— or $C_1$–$C_{12}$alkylphenyl—$C_nH_{2n}SO_2$—, or phenyl—$C_nH_{2n}$—, phenyl—$C_nH_{2n}O$—, phenyl—$C_nH_{2n}S$— or phenyl—$C_nH_{2n}SO_2$— in which n is a number from 1 to 4, in particular 1 or 2 and especially 1. Some examples are phenyl, phenoxy, phenylthio, benzyl, benzyloxy, benzylthio, methylphenyl, methylphenoxy, methylphenylthio, methylbenzyl, methylbenzyloxy and methylbenzylthio.

As secondary amino, $R^2$ preferably contains 2 to 18, in particular 2 to 12, and especially 2 to 8, C atoms. The secondary amino can have the formula —$NR^5R^6$ in which $R^5$ and $R^6$ independently of one another are linear or branched $C_1$–$C_{18}$alkyl, in particular $C_1$–$C_{12}$alkyl and especially $C_1$–$C_6$alkyl, cyclopentyl, cyclohexyl, phenyl, benzyl, $C_1$–$C_6$alkylphenyl or $C_1$–$C_6$alkylbenzyl, or $R^5$ and $R^6$ together are tetramethylene, pentamethylene or 3-oxa-1,5-pentylene. Some examples are dimethylamino, diethylamino, ethylmethylamino, dibutylamino, dioctylamino, methyldodecylamino, didodecylamino, methyloctadecylamino, phenylmethylamino, benzylmethylamino, pyrrolino, piperidino and morpholino.

As trialkylsilyl or trialkoxysilyl, $R^2$ preferably contains 3 to 12 C atoms, in particular 3 to 8 C atoms. Alkyl and alkoxy groups have been mentioned above. Some examples are trimethylsilyl, triethylsilyl, dimethylethylsilyl, tributylsilyl, dimethylbutylsilyl, dimethyl-(1,1,2,2-tetramethylethyl)silyl, dimethyloctylsilyl, trimethoxysilyl and triethoxysilyl.

A preferred group of compounds according to the invention is constituted by those in which $R^2$ is —F, —CN, —$CF_3$, —Br, —Cl, $C_1$–$C_{18}$alkyl or $C_2$–$C_{12}$alkenyl, $C_1$–$C_{18}$alkoxy, $C_1$–$C_{18}$alkylthio, $C_1$–$C_{18}$alkylsulfonyl, phenyl, $C_1$–$C_{12}$alkylphenyl, phenyl—$C_nH_{2n}$—, $C_1$–$C_{12}$alkylphenyl—$C_nH_{2n}$—, phenoxy, phenylthio or phenylsulfonyl, $C_1$–$C_{12}$alkylphenoxy, $C_1$–$C_{12}$alkylphenylthio or $C_1$–$C_{12}$alkylphenylsulfonyl, phenyl—$C_nH_{2n}$—O—, phenyl—$C_nH_{2n}$—S— or phenyl—$C_nH_{2n}$—$SO_2$—, $C_1$–$C_{12}$alkylphenyl—$C_nH_{2n}$—O—, $C_1$–$C_1$-

2alkylphenyl—$C_nH_{2n}$—S— or $C_1$-$C_{12}$alkylphenyl—$C_nH_{2n}$—$SO_2$—, in which n is a number from 1 to 4, secondary amino having 2 to 18 C atoms, or trialkylsilyl or trialkoxysilyl having 3 to 12 C atoms.

In a particularly preferred embodiment, $R^2$ is —F, —Cl, —Br, —$CF_3$, $C_1$-$C_{12}$alkyl, $C_1$-$C_{12}$alkoxy, $C_1$-$C_{12}$alkylthio, benzylthio or $C_1$-$C_{12}$alkylbenzylthio or secondary amino having 2 to 12 C atoms.

The invention also relates to a process for the preparation of compounds of the formula I, which comprises cyclizing a compound of the formula II

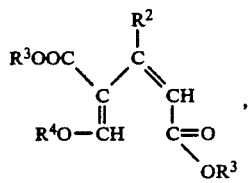

in which $R^2$ and $R^3$ are as defined above and $R^4$ is $C_1$-$C_4$alkyl, in the presence of a strong, anhydrous acid, to give a compound of the formula I.

In formula II, $R^4$ is particularly methyl or ethyl.

The invention also relates to the compounds of the formula II. They can be prepared in a manner analogous to the process described in U.S. Pat. No. 4,617,151 by reacting propene-1,3-dicarboxylic acid diesters of the formula III

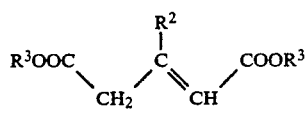

with formic acid esters $HCOOR^4$ in the presence of $TiCl_4$ or an alkali metal hydride or alcoholate. Examples of suitable alkali metals are Li, Na and K and Examples of alcohols are $C_1$-$C_4$alkanols, for example methanol and ethanol.

The compounds of the formula III can be prepared by various methods. The starting compound is, for example, the known ketodicarboxylic acid diester of the formula IV

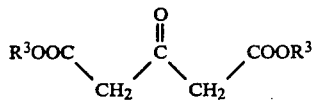

Compounds of the formula III in which $R^2$ is an alkoxy radical are obtained by enolization with alkylating agents, for example dialkyl sulfates, orthoformic acid esters in the presence of $FeCl_3$, or alkyl halides.

The reaction of the compound of the formula IV with, for example, $PCl_5$ or diethylaminosulfur trifluoride (DAST) gives compounds of the formula III in which $R^2$ is Cl or F. These can be reacted with alkali metal salts of organic mercapto compounds or sulfonyl compounds (examples of alkali metal are Li, Na or K) to give compounds of the formula III in which $R^2$ is one of the thio radicals or sulfonyl radicals defined above.

Compounds of the formula III in which $R^2$ is Cl can be dehydrochlorinated in a customary manner to give allenedicarboxylic acid esters of the formula V

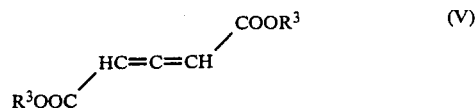

Reacting the latter with $NH_4HF_2$ or (n-butyl)$_4NH_2F_3$ also leads to compounds of the formula III in which $R^2$ is F. Compounds of the formula III are obtained by means of organometallic reagents $R^2Z$ ($R^2$ is not halogen or —$CF_3$) in which Z is preferably an alkali metal, in particular Li, Na or K, followed by hydrolysis. If $R^2$ is a hydrocarbon radical, it is preferable to use an inorganic copper salt, for example copper(I) halides or in particular CuCN, concomitantly in the reaction with $R^2Z$. Compounds of the formula III substituted by secondary amines are also obtained by direct reaction with secondary amines. The reaction with $R^2Z$ is advantageously carried out in a polar, aprotic solvent. Examples are ethers, especially diethyl ether, dibutyl ether, tetrahydrofuran, dioxane or ethylene glycol diethyl ether. The reaction temperature is advantageously —20° to —100° C.

Compounds of the formula I in which $R^1$ and/or $R^2$ are —$CF_3$ are obtained by fluorinating, for example using $SF_4$/HF, the corresponding carboxylic acid alkyl esters, in particular the methyl or ethyl ester.

Compounds of the formula I in which $R^2$ is a thio or sulfonyl radical can also be prepared by appropriate substitution of α-pyrones of the formula I in which $R^2$ is Cl or Br.

The cyclization of compounds of the formula II can also be carried out by the process described in specification U.S. Pat. No. 4,617,151. It is advantageous to carry out the cyclization using anhydrous formic acid or polyphosphoric acid without a solvent. The temperature for this reaction is advantageously 50° to 250° C.

The compounds of the formula I can be reacted with benzo-1,4-quinone to give naphthoquinones of the formula VI

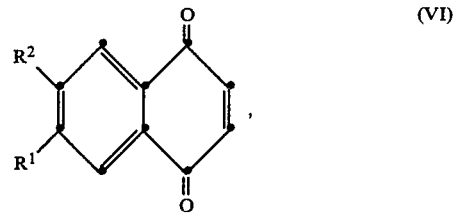

in which $R^1$ and $R^2$ are as defined in formula I. The invention also relates to these naphthoquinones.

Preferably, $R^2$ in formula VI is —$CF_3$, F, —Cl, —Br, $C_1$-$C_{18}$alkyl, $C_1$-$C_{18}$alkoxy, $C_1$-$C_{18}$alkylthio, $C_1$-$C_{18}$alkylsulfonyl, phenoxy, phenylthio, phenylsulfonyl, $C_1$-$C_{12}$alkylphenoxy, $C_1$-$C_{12}$alkylphenylthio, $C_1$-$C_{12}$alkylphenylsulfonyl, benyloxy, benzylthio, benzylsulfonyl, $C_1$-$C_{12}$alkylbenzyloxy, $C_1$-$C_{12}$alkylbenzylthio or $C_1$-$C_{12}$alkylbenzylsulfonyl. In a particular embodiment, $R^1$ is —$CH_3$ or —$COOR^3$ and $R^2$ is —$CF_3$, —F, —Cl, $C_1$-$C_{12}$alkyl, $C_1$-$C_{12}$alkoxy, $C_1$-$C_{12}$alkylthio, $C_1$-$C_{12}$alkylsulfonyl or benzylthio and $R^3$ is $C_1$-$C_4$alkyl.

The compounds of the formula I and VI are valuable intermediates for the preparation of substituted anthracene-5,12-diones, from which substituted tetrathiotetracenes and/or tetraselenotetracenes can be obtained (cf.

U.S. Pat. No. 4,617,151). Electrically conductive charge-transfer complexes (CT complexes) can be prepared from such chalkogenated tetracenes by means of electron acceptors. They can be attached to polymers, for example incorporated into polymers as side groups (cf. U.S. Pat. No. 4,617,151) by means of their functional groups. The CT complexes are also suitable for the production of, for example, antistatic coatings of photographic film elements, magnetic tapes, electrophotographic film elements and electronic components (see U.S. Pat. No. 3,634,336). The chalkogenated tetracenes also exhibit electrochromic properties; they can be used for electrochromic displays. They are also suitable for use as laser-optical data storage [Nach. Chem. Techn. Lab. 35, pages 255 et seq. (1987)] and as anode material in organic solid state batteries (EP-A 0,090,598). CT complexes of unsubstituted or substituted tetrathiotetracenes or tetraselenotetracenes can also be incorporated into thermoplastic, thermosetting or elastomeric polymers in order to achieve antistatic properties. This is advantageously effected, for example, by dissolving these tetrathiotetracenes or tetraselenotetracenes, together with a soluble polymer or a precursor thereof and an electron acceptor, for example an agent which forms halogen (organic halogenated compounds, for example bromoform, trichlorobromomethane, tetrabromomethane, hexachloropropane, perchlorobutadiene, 1,3-dichloro-2-butene, 1,4-dichloro-2-butene, 1,4-bis-(trichloromethyl)-benzene, iodoacetonitrile, iodoform, tetrachloroethylene, perchlorocyclobutadiene, N-chlorosuccinimide, N-bromosuccinimide or N-iodosuccinimide), if appropriate together with a further inert solvent, and removing by evaporation at an elevated temperature the excess agent which forms halogen and the solvent. The composition formed contains, in the polymer, a network of needle-shaped crystals of the CT complex, if the chalkogenated tetracene is unsubstituted or contains small substituents (for example F, $CH_3$ or $CF_3$). Compositions of this type exhibit a high electrical conductivity. This can be improved further if a substituted tetrathiotetracene or tetraselenotetracene prepared from the compounds of the formula I and which does not form such a network and which is present in finely divided form in the polymer matrix is concomitantly used, since substituted tetrathiotetracenes or tetraselenotetracenes of this type have no tendency or only a slight tendency to crystallize in the polymer.

The compounds of the formula I are valuable diene components for DielsAlder reactions, for which a variety of dieneophiles can be used. If substituted or unsubstituted 1,4-quinones are used, for example benzo-1,4-quinone, naphthalene-1,4-quinone or anthracene-1,4-quinone, quinones enlarged by a ring are obtained (see, for example, EP-A 0,195,743). Substituted naphthacene-5,12-diones can also be obtained directly by reacting substituted or unsubstituted naphthalene-1,4-quinones with benzocyclobutenes which are substituted in the 1-position and 2-position by bromine and/or iodine. Anthraquinones and naphthacene diones can be used, for example, as photosensitizers (cf. U.S. Pat. No. 3,941,759) or photoinitiators for the polymerization of ethylenically unsaturated compounds, in particular naphthacene-5,12-diones which are at least substituted by a thio radical in the 2-position. Naphthacene quinones can also be used in electrochromic display elements (Japanese Preliminary Published Specification 61-43,680).

The following examples illustrate the invention.

EXAMPLE 1

Ethyl 4-butyl-2H-2-oxopyran-5-carboxylate (a) Diethyl 2-butylprop-1-ene-1,3-dicarboxylate 10 g of CuCN are suspended in 200 ml of toluene and the toluene is removed by distillation at 35° C. on a rotary evaporator. The procedure is repeated again. The vacuum is replaced by argon, 200 ml of tetrahydrofuran (THF) are added and the suspension is cooled to −70° C. 125 ml of a hexane solution of 12.8 g of n-butyllithium are added dropwise at this temperature. A yellow solution is formed, with an exothermic reaction.

After 15 minutes of stirring, 13.8 g of diethyl allenedicarboxylate in 100 ml of THF are added dropwise at −50° C. A red solution is formed, which is stirred for a further 2 hours at −20° C. After 2 hours the reaction mixture is warmed to room temperature. 500 ml of a buffer solution (27 g of $NH_4Cl$ dissolved in 100 ml of concentrated ammonia solution) are then added to the reaction mixture. The reaction mixture is stirred at room temperature for 15 minutes, diluted with 500 ml of saturated NaCl solution and extracted twice with 400 ml of diethyl ether. The combined extracts are dried by means of $Na_2SO_4$ and the diethyl ether is removed by distillation on a rotary evaporator. The distillation residue (16.7 g) is chromatographed over 300 g of $SiO_2$ (mobile phase $CH_2Cl_2$; 0.3–0.5 bar excess pressure): yield 12.94 g.

Distillation of the product in a kugelrohr oven at 120° C./$1.3 \times 10^{-2}$ mbar gives a colourless oil.

(b) Diethyl 2-butyl-3-ethoxymethylenylprop-1-ene-1,3-dicarboxylate 11.34 g (0.06 mol) of $TiCl_4$ in 15 ml of $CCl_4$ are added dropwise, with stirring and at 0° C., to 120 ml of THF. After 15 minutes 4.44 g (0.06 mol) of ethyl formate followed by 3.63 g (0.015 mol) of diethyl 2-butylprop-1-ene-1,3-dicarboxylate are added to the resulting yellow complex. After 15 minutes of stirring, 12.12 g (0.012 mol) of N-methylmorpholine in 21 m of THF are added dropwise and in the course of 30 minutes to the reaction mixture at 0°–5° C. The reaction mixture is stirred at room temperature for 24 hours and is then introduced into 150 ml of $CH_2Cl_2$ and 100 ml of saturated $KHCO_3$ solution. After stirring for 30 minutes, the precipitated titanium salt is filtered off. The $CH_2Cl_2$ solution is separated from the water in the filtrate. The $CH_2Cl_2$ phase is washed with water, dried with $Na_2SO_4$ and evaporated, and residual N-methylmorpholine is removed at 100° C./1.3 mbar. The oily residue is filtered through 150 g of $SiO_2$ (mobile phase $CH_2Cl_2$; 0.3 bar excess pressure). The crude product obtained is chromatographed (silica gel; mobile phase: $CH_2Cl_2$). 1.95 g (43.5%) of a pale yellow oil are obtained.

(c) Ethyl 4-butyl-2H-2-oxopyran-5-carboxylate 1.4 g (0.0047 mol) of diethyl 2-butyl-3-ethoxymethylenylprop-1-ene-1,3-dicarboxylate and 14 ml of formic acid are heated for 20 minutes in a bath preheated to 110° C. The formic acid is then removed by distillation at 50° C. under a water pump vacuum. The residue is dissolved in 20 ml of $CH_2Cl_2$, and the solution is washed with 10 ml of saturated NaCl solution, dried with $Na_2SO_4$ and evaporated to dryness. Yield: 0.95 g (90.5%) of an oily product.

EXAMPLE 2

Ethyl 4-benzylthio-2H-2-oxopyran-5-carboxylate (a) Diethyl 2-benzylmercaptoprop-1-ene-1,3-dicarboxylate 1.84 g of Na are dissolved in 200 ml of methanol. 10.91 g of benzyl mercaptan are added, and the methanol is removed by distillation in vacuo. The distillation residue is evaporated twice with 100 ml of toluene. The residue is dissolved in 120 ml of dimethyl sulfoxide (DMSO), and 17.64 g of diethyl $\beta$-chloroglutaconate are added to the solution. The reaction mixtures warms up to 53° C. It is stirred overnight at room temperature. The DMSO is removed by distillation in vacuo at 80° C./1.3 mbar. The residue is taken up in $CH_2Cl_2$, and the solution is washed with acidified (HCl) water. Drying with $Na_2SO_4$ and removing the $CH_2Cl_2$ by distillation gives 24.15 g of product (97.9%) in the form of a golden-yellow oil.

(b) Diethyl 2-benzylmercapto-3-ethoxymethylenoprop-1-ene-1,3-dicarboxylate 105.2 g (0.557 mol) of $TiCl_4$ in 140 ml of $CCl_4$ are added dropwise, with stirring and at 0° C., to 1115 ml of THF. First 41.2 g (0.557 mol) of ethyl formate and then 43 g (0.139 mol) of diethyl 2-benzylmercaptoprop-1-ene-1,3-dicarboxylate are added at the same temperature. After 15 minutes a solution of 112.9 g (1.115 mol) of N-methylmorpholine in 195 ml of THF is added dropwise in the course of 30 minutes at the same temperature. The reaction mixture is then stirred at room temperature overnight and is then introduced into a mixture of 1000 ml of $CH_2Cl_2$ and 2000 ml of saturated $NaHCO_3$ solution. After being stirred for 30 minutes, the mixture is filtered. The $CH_2Cl_2$ phase of the filtrate is separated from the aqueous phase, washed again twice with 300 ml of water, dried with $Na_2SO_4$ and concentrated in vacuo. 47.66 g (94%) of an orange oil are obtained.

(c) Ethyl 4-benzylthio-2H-2-oxopyran-5-carboxylate 47.66 g (0.130 mol) of diethyl 2-benzylmercapto-3-ethoxymethylenylprop-1-ene-1,3-dicarboxylate are dissolved in 481 ml of formic acid and the mixture is heated for 20 minutes in a bath preheated to 110° C. The formic acid is then removed by vacuum distillation. The residue is taken up in 500 ml of $CH_2Cl_2$ and is washed with aqueous NaCl solution and then with water. After the solution has been dried with $Na_2SO_4$, the solvent is removed by vacuum distillation. The distillation residue crystallizes out [25.9 g (68.7%)]. The melting point (recrystallized from ethanol) is 99°–101° C.

EXAMPLE 3

Ethyl 4-chloro-2H-2-oxopyran-5-carboxylate (a) Diethyl 1-ethoxy-3-chlorobutadiene-2,4-dicarboxylate 7.56 g (0.04 mol) of $TiCl_4$, dissolved in 10 ml of $CCl_4$, are added dropwise at 0° C. to 80 ml of THF. First 2.96 g (0.04 mol) of ethyl formate and then 2.2 g (0.01 mol) of $\beta$-chloroglutaconic acid are added to the resulting yellow complex. After 15 minutes a solution of 8.08 g (0.08 mol) of N-methylmorpholine in 14 ml of THF is added dropwise at 0° C. in the course of 30 minutes. The reaction mixture is stirred overnight at room temperature. The solvent is then removed from the reaction mixture by vacuum distillation at 35° C. The residue is suspended in 200 ml of $CH_2Cl_2$, 200 ml of water containing 11 g of $NaHCO_3$ are added and the mixture is filtered after being stirred for 1 hour. The two phases of the filtrate are separated and the organic solution is concentrated under a water pump vacuum. The residue is filtered through a column of 35 g of silica gel (mobile phase: $CH_2Cl_2$). 1.92 g (69.6%) of an oily product remain after the mobile phase has been removed by distillation.

(b) Ethyl 4-chloro-2H-2-oxopyran-5-carboxylate 74.12 g (0.268 mol) of diethyl 1-ethoxy-3-chlorobutadiene-2,4-dicarboxylate, dissolved in 700 ml of formic acid, are heated for 30 minutes in a bath preheated to 110° C., and are cooled and evaporated to dryness in vacuo at 50° C. The residue is taken up in 250 ml of $CH_2Cl_2$, the solution is washed with water until neutral, dried with $Na_2SO_4$ and then concentrated. The distillation residue is chromatographed over 1300 g of silica gel (mobile phase: 99:1 $CH_2Cl_2$/acetone, 0.3 bar excess pressure). After concentration, the distillation residue (29 g) is crystallized from a mixture of 12 ml of diethyl ether and 10 ml of hexane at −20° C. Yield 22.79 g (42%), melting point: 38°–39° C.

EXAMPLE 4

Ethyl 4-ethoxy-2-oxo-2H-pyran-5-carboxylate (a) Diethyl 1,3-ethoxybutadiene-2,4-dicarboxylate A solution of 130.41 g (0.69 mol) of $TiCl_4$ in 170 ml of $CCl_4$ is added dropwise, with stirring, to 1380 ml of THF. During this addition, the temperature is kept at 0° C. by cooling. First 36.72 g (0.17 mol) of ethyl 3-ethoxyglutaconate and then 51.06 g (0.69 mol) of ethyl formate are introduced and, finally, 139.38 g (1.38 mol) of N-methylmorpholine in 241 ml of THF are added dropwise at 0° C. in the course of 0.5 hour. The reaction mixture is stirred overnight at room temperature and is then introduced into a solution of 150 g of $NaHCO_3$ in 1200 ml of $H_2O$ and 1200 ml of $CH_2Cl_2$, and the mixture is stirred for 2 hours. The precipitated titanium dioxide is filtered off with suction. The filtrate is then extracted with 3×300 ml of methylene chloride. The combined methylene chloride extracts are dried with $Na_2SO_4$ and concentrated. The crude product which remains is chromatographed over a column filled with 1300 g of silica gel 60 (mobile phase 19:1 $CH_2Cl_2$/acetone, 0.3 bar excess pressure). 31.9 g (67.6%) of an oily product are obtained after the mobile phase has been removed.

(b) Ethyl 4-ethoxy-2-oxo-2H-pyran-5-carboxylate 26 g (0.0908 mol) of diethyl 1,3-ethoxybutadiene-2,4-dicarboxylate and 156 g of polyphosphoric acid are heated at 140° C. for 30 minutes, and the mixture is diluted with 1000 ml of water and extracted first with 1000 ml of $CH_2Cl_2$ and then with 3 times 200 ml of $CH_2Cl_2$. The extracts are washed with saturated NaCl solution until they are at pH 5. The solution is then dried with $Na_2SO_4$ and evaporated. The distillation residue is chromatographed over 160 g of silica gel 60 (19:1 $CH_2Cl_2$/acetone, 0.3 bar excess pressure). After the mobile phase has been removed, 11.3 g (58.7%) of crystals of melting point 86°–89° C. are obtained.

EXAMPLE 5

4,5-Bis-trifluoromethyl-2-oxo-2H-pyran 50 g (0.0208 mol) of diethyl 2-oxo-2H-pyran-4,5-dicarboxylate, 170 g (1.57 mol) of $SF_4$ and 300 g (15 mol) of HF are heated in an autoclave at 150° C. for 10 hours. The reaction mixture is diluted with 500 ml of $CH_2Cl_2$ and is poured into 1500 ml of water. The pH is adjusted to a value of 7.5 by adding $NaHCO_3$ gradually, with stirring. The organic phase is separated off, dried over $Na_2SO_4$ and filtered, and the solvent is removed by vacuum distillation at 50° C. The distillation residue is extracted five times with 100 ml of n-pentane, and the pentane solution is concentrated. Distillation at 68°–70° C./13 mbar gives 18.62 g (38.5%) of 4,5-bis-trifluoromethyl-2-oxo-2H-pyran.

EXAMPLE 6

Ethyl 4-fluoro-2H-2-oxopyran-5-carboxylate (a) Diethyl 3-fluoropent-2(E)-enedicarboxylate A mixture of tetrabutylammonium dihydrogentrifluoride (prepared from 30 mmol of tetrabutylammonium fluoride, KF and HF), 20 ml of 1,2-dichloroethane and 15 mmol (2.76 g) of diethyl allenedicarboxylate is heated under reflux for 1 hour. The mixture is then diluted with methylene chloride and washed slowly with ice water, sodium bicarbonate and ammonium chloride solution, dried with $Na_2SO_4$ and evaporated. The crude product is flash-filtered over 50 g of silica gel using 500 ml of 4:1 hexane/ethyl acetate and distilled under a high vacuum. 1.79 g (59% of theory) of the desired product are obtained; boiling point: 50°–55° C./0.06 mbar.

(b) Diethyl-1-ethoxy-3-fluorobutadiene-2,4-dicarboxylate

A mixture of 3.78 g (0.02 mol) of $TiCl_4$ in 5 ml of $CCl_4$ is added dropwise, at 0° C. and with stirring, to 40 ml of tetrahydrofuran (THF). 1.02 g (0.005 mol) of diethyl 3-fluoropent-2(E)-enedicarboxylate and 1.48 g (0.02 mol) of ethyl formate are then added dropwise. After 15 minutes, a solution of 4.04 g (0.04 mol) of N-methylmorpholine in 7 ml of THF is added dropwise at 0°–5° C. The reaction mixture is stirred for 17 hours at room temperature and is then stirred into a mixture of 50 ml of saturated $KHCO_3$ solution and 100 ml of $CH_2Cl_2$. The precipitated titanium salt is filtered off with suction, and the organic phase is separated off from the aqueous phase. The aqueous phase is extracted once more with 100 ml of $CH_2Cl_2$, and the combined organic phases are dried with $Na_2SO_4$ and concentrated. The distillation residue is freed from excess N-methylmorpholine at 85° C./1.3 mbar, and the residue is chromatographed over 150 g of $SiO_2$ (mobile phase 19:1 $CH_2Cl_2$/acetone). This gives 1 g (77% of theory) of the product (an orange oil).

(c) Ethyl 4-fluoro-2H-2-oxo-pyran-5-carboxylate 6 g of PPA (polyphosphoric acid) are added to 1 g (0.0038 mol) of diethyl 1-ethoxy-3-fluorobutadiene-2,4-dicarboxylate, and the mixture is stirred for 30 minutes at 80° C., diluted with 20 ml of water and extracted 3 times with 20 ml of $CH_2Cl_2$. The $CH_2Cl_2$ phase is washed with $H_2O$, dried ($Na_2SO_4$) and concentrated. The distillation residue is chromatographed over silica gel (mobile phase 99:1 $CH_2Cl_2$/acetone). Evaporating the solvent leaves a residue of 0.2 g (28% of theory) of the pure product (an orange oil).

EXAMPLE 7

Ethyl 4-methylsulfonyl-2H-2-oxopyran-5-carboxylate (a) Diethyl 3-methylsulfonylpent-2-enedicarboxylate A mixture of 0.44 g (0.002 mol) of diethyl 3-chloropent-2-enedicarboxylate and 0.3 g (0.003 mol) of sodium sulfinate in 1.5 ml of dimethylformamide (DMF) is stirred at 100° C. for 1 hour, and DMF is then distilled off in vacuo at 110° C./1.3 mbar. The residue is mixed with 0.5 ml of water. The fraction insoluble in water crystallizes out and is filtered off with suction and washed with water. The crude crystalline material is chromatographed over 12 g of silica gel (mobile phase 99:1 $CH_2Cl_2$/acetone). This gives 0.43 g (81.44% of theory) of the product; melting point: 54°–57° C.

(b) Diethyl 1-ethoxy-3-methylsulfonylbutadiene-2,4-dicarboxylate

A solution of 4.53 g (0.024 mol) of $TiCl_4$ in 6 ml of $CCl_4$ is added dropwise to 48 ml of THF with ice cooling (0°–5° C). First 1.77 g (0.024 mol) of formic acid ester and then 1.58 g (0.006 mol) of diethyl 3-methylsulfonylpent-2-enedicarboxylate are added dropwise at the same temperature, with stirring. After 30 minutes 4.86 g (0.048 mol) of N-methylmorpholine in 8.5 ml of THF are added at 0°–5° C. in the course of 1 hour. The reaction mixture is then stirred for 20 hours at 25° C., diluted with 100 ml of $CH_2Cl_2$ and poured into 30 ml of saturated $KHCO_3$ solution. The titanium salt is filtered off with suction and the organic phase is separated from the filtrate. The aqueous phase is extracted with a further 50 ml of $CH_2Cl_2$. The combined $CH_2Cl_2$ extracts are washed with saturated NaCl solution, dried with $Na_2SO_4$ and concentrated. The distillation residue is chromatographed (200 g of silica gel; mobile phase 19:1 $CH_2Cl_2$/acetone). This gives 1.17 g (60.94%) of the product.

(c) Ethyl 4-methylsulfonyl-2-oxo-2H-pyran-5-carboxylate 1.2 g of sodium methylsulfinate are introduced into a solution of 2.02 g of ethyl 4-chloro-2-oxo-2H-pyran-5-carboxylate in DMF, and the mixture is stirred for 2 hours at room temperature. The reaction mixture is diluted with $CH_2Cl_2$ and extracted with saturated aqueous NaCl solution. The organic phase is dried with $Na_2SO_4$ and evaporated. The distillation residue which has crystallized out is mixed with ether, filtered off with suction and washed with ether. Yield 1.4 g (56.9% of theory); melting point: 95°–97° C.

EXAMPLE 8

6,7–Bis-trifluoromethyl-1,4-naphthoquinone 23.47 g (0.1011 mol) of 4,5-bis-trifluoromethyl-2-oxo-2H-pyran, 54.62 g (0.5053 mol) of 1,4-benzoquinone and 26.30 g (0.3026 mol) of $MnO_2$ in 225 ml of 1,2-dichlorobenzene are heated at 180° C. for 12 hours. The reaction mixture is then diluted with 200 ml of $CHCl_3$ and filtered through Hyflo ®. After the chloroform has been removed by distillation, the distillation residue is chromatographed over a column packed with 1300 g of $SiO_2$ (mobile phase: first cyclohexane and then $CHCl_3$; 0.3 bar excess pressure). Yield 17.94 g (60.3%), melting point: 91°–94° C.

EXAMPLE 9

Ethyl 6-ethoxy-1,4-naphthoquinone-7-carboxylate 0.42 g (0.002 mol) of ethyl 4-ethoxy-2-oxo-2H-pyran-5-carboxylate, 1.08 g (0.01 mol) of 1,4-benzoquinone and 0.54 g (0.0062 mol) of $MnO_2$ in 4.8 ml of dichlorobenzene are heated at 180° C. for 12 hours. The resulting reaction mixture is chromatographed over a column of 30 g of silica gel 60 (mobile phase 99:1 $CH_2Cl_2$/acetone, 0.3 bar excess pressure). This gives 0.41 g (75.9%) of crystals of melting point 60°–62° C.

USE EXAMPLE (a) Preparation of 2,3-di-(trifluoromethyl)-5,6,11,12-tetrathiotetracene 25 mmol of 6,7-bis-trifluoromethyl-1,4-naphthquinone, approx. 37 mmol of 1,2-dibromobenzocyclobutene [see J. Am. Chem. Soc. 79, pages 1701 et seq. (1957)] containing a little 1-bromo-2-iodobenzocyclobutene and 100 ml of xylene are kept under reflux for 16 hours in a water separator. The reaction mixture is cooled and the precipitate is filtered off and washed with xylene. The crystalline 2,3-di-(trifluoromethyl)-naphthacene-5,12-dione is obtained in a yield of 5.82 g (71%), melting point >280° C.

1.65 mmol of 2,3-di-(trifluoromethyl)-naphthacene-5,12-dione, 5 ml of ethyl acetate, 4.96 mmol of potassium acetate and 3 ml of acetic anhydride are hydrogenated for 35 minutes at 20°–25° C., with the addition of 0.1 g of Pd/C (5%). The reaction mixture is filtered and the residue is washed three times with $CH_2Cl_2$. The filtrates are evaporated and the residue is recrystallized from $CHCl_2$/pentane. 2,3-Di-(trifluoromethyl)-5,12-diacetoxynaphthacene is obtained in a yield of 0.45 g (70%), melting point 149°–153° C.

0.61 mmol of the diacetoxynaphthacene, 2.43 milliequivalents of $S_8$ and 0.01 mmol of p-toluenesulfonic acid in 35 ml of 1,2,4-trichlorobenzene are refluxed for 20 hours under a gentle stream of argon in a 100 ml flask equipped with a reflux condenser and a gas inlet tube. After cooling, the solvent is removed by evaporation under a high vacuum, the residue is boiled with hexane, and the black powder is filtered off and dried at 60° C. under a high vacuum. 79% of crude product are obtained. It is sublimed at 190° C. ($1.3 \times 10^{-4}$ mbar), to give 75.6 mg (30%) of pure 2,3-di-(trifluoromethyl)-5,6,11,12-tetrathiotetracene in the form of small black needles. Mass spectrum: $M^+ = 488$; $\lambda_{max}$ (1,2,4-trichlorobenzene): 755 nm.

(b) Electrochromism 1 mg of 2,3-di-(trifluoromethyl)-5,6,11,12-tetrathiotetracene and 100 mg of $LiClO_4$, dissolved in 5 ml of acetone, are introduced into the anode side of an electrochromic cell consisting of a Teflon membrane and an anode and cathode made of ITO glass both at a distance of 0.5 mm, and a solution of 1 mg of 2,3-di-(trifluoromethyl)-5,6,11,12-tetrathiotetracene perchlorate (CT complex, for preparation see U.S. Pat. No. 3,634,336) and 100 mg of $LiClO_4$ in 5 ml of acetone are introduced into the cathode side. After a voltage of 2 volts has been applied, the colours change in the course of a few seconds from green to red-violet on the anode side and from red-violet to green on the cathode side. The original colours are obtained in both halves of the cell on reversing the polarity of the voltage. The same effect is observed if nitrobenzene or dimethylformamide is used as the solvent.

What is claimed is:

1. A compound of the formula I

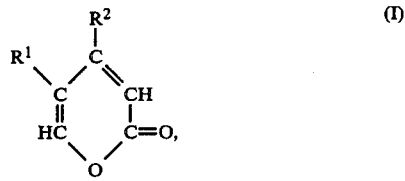

in which $R^1$ is $—CF_3$ or $—COOR^3$ and $R^3$ is the radical of a $C_1-C_{18}$ alcohol diminished by a hydroxyl group, and $R^2$ is —F, —Br, —Cl, —CN, $—CF_3$, $C_1-C_{18}$alkyl, $C_2-C_{18}$alkenyl, $C_2-C_{18}$alkynyl, $C_1-C_{18}$alkoxy, $C_1-C_{18}$alkylthio, $C_1-C_{18}$alkylsulfonyl, $C_6-C_{16}$aryl, $C_7-C_{24}$alkaryl, $C_7-C_{12}$aralkyl, $C_8-C_{24}$alkaralkyl, $C_6-C_{16}$aryloxy, $C_6-C_{16}$arylthio, $C_6-C_{16}$arylsulfonyl, $C_7-C_{24}$alkaryloxy, $C_7-C_{20}$alkarylthio, $C_7-C_{24}$alkarylsulfonyl, $C_7-C_{12}$aralkyloxy, $C_7-C_{12}$aralkylthio, $C_7-C_{12}$aralkylsulfonyl, $C_8-C_{24}$alkaralyloxy, $C_8-C_{24}$alkaralylthio, $C_8-C_{24}$alkaralylsulfonyl, secondary amine having 2 to 24 C atoms or trialkylsilyl or trialkoxysilyl each of which has 3 to 18 C atoms wherein aryl is phenyl or naphthyl.

2. A compound according to claim 1, in which $R^3$ is $C_1-C_{18}$alkyl.

3. A compound according to claim 2, in which $R^3$ is methyl or ethyl.

4. A compound according to claim 1, in which $R^2$ is —F, —CN, $—CF_3$, —Br, —Cl, $C_1-C_{18}$alkyl or $C_2-C_{12}$alkenyl, $C_1-C_{18}$alkoxy, $C_1-C_{18}$alkylthio, $C_1-C_{18}$alkylsulfonyl, phenyl, $C_1-C_{12}$alkylphenyl, phenyl—$C_nH_{2n}$—, $C_1-C_{12}$alkylphenyl—$C_nH_{2n}$—, phenoxy, phenylthio or phenylsulfonyl, $C_1-C_{12}$alkylphenoxy, $C_1-C_{12}$alkylphenylthio or $C_1-C_{12}$alkylphenylsulfonyl, phenyl—$C_nH_{2n}$—O—, phenyl—$C_nH_{2n}$—S— or phenyl—$C_nH_{2n}$—$SO_2$—, $C_1-C_{12}$alkylphenyl—$C_nH_2$—O—, $C_1-C_{12}$alkylphenyl—$C_nH_{2n}$—S— or $C_1-C_{12}$alkylphenyl—$C_nH_{2n}$—$SO_2$—, in which n is a number from 1 to 4, secondary amino having 2 to 18 C atoms, or trialkylsilyl or trialkoxysilyl having 3 to 12 C atoms.

5. A compound according to claim 1, in which $R^2$ is —F, —Cl, —Br, $—CF_3$, $C_1-C_{12}$alkyl, $C_1-C_{12}$alkoxy, $C_1-C_{12}$alkylthio, benzylthio or $C_1-C_{12}$alkylbenzylthio or secondary amino having 2 to 12 C atoms.

* * * * *